(12) United States Patent
Fritz et al.

(10) Patent No.: US 7,333,197 B2
(45) Date of Patent: Feb. 19, 2008

(54) RAMAN DETECTION BASED FLOW CYTOMETER

(75) Inventors: Bernard S. Fritz, Eagen, MN (US); Aravind Padmanabhan, Plymouth, MN (US); Cleopatra Cabuz, Edina, MN (US)

(73) Assignee: Honeywell International Inc., Morristown, NJ (US)

( * ) Notice: Subject to any disclaimer, the term of this patent is extended or adjusted under 35 U.S.C. 154(b) by 295 days.

(21) Appl. No.: 10/991,001

(22) Filed: Nov. 17, 2004

(65) Prior Publication Data

US 2006/0103840 A1   May 18, 2006

(51) Int. Cl.
*G01N 21/00* (2006.01)

(52) U.S. Cl. ............... 356/338; 356/213; 356/244; 356/246

(58) Field of Classification Search ............ 356/338, 356/213, 244, 246
See application file for complete search history.

(56) References Cited

U.S. PATENT DOCUMENTS

| | | | |
|---|---|---|---|
| 3,850,525 | A | 11/1974 | Kaye |
| 4,071,298 | A | 1/1978 | Falconer et al. |
| 5,245,405 | A | 9/1993 | Mitchell et al. |
| 5,949,532 | A | 9/1999 | Schrof et al. |
| 6,382,228 | B1 | 5/2002 | Cabuz et al. |
| 6,549,275 | B1 | 4/2003 | Cabuz et al. |
| 6,597,438 | B1 | 7/2003 | Cabuz et al. |
| 2002/0150938 | A1* | 10/2002 | Kneip et al. ............ 356/1 |
| 2003/0142291 | A1* | 7/2003 | Padmanabhan et al. ....... 356/39 |
| 2004/0142484 | A1* | 7/2004 | Berlin et al. .............. 436/171 |
| 2006/0023207 | A1* | 2/2006 | Cox et al. ................ 356/338 |

FOREIGN PATENT DOCUMENTS

DE           19946110 C1    2/2001

OTHER PUBLICATIONS

Katrin Kneip et al., Surface-enhanced Raman Spectroscopy in Single Living Cells Using Gold Nanaparticles, 2002, Society for Applied Spectroscopy, vol. 56, No. 2, pp. 1-2.*
Milton Kerker, Elastic and Inelastic Light Scattering in Flow Cytomery, Jan. 19, 1983, pp. 1-10.*

(Continued)

*Primary Examiner*—Gregory J. Toatley, Jr.
*Assistant Examiner*—Abdullahi Nur
(74) *Attorney, Agent, or Firm*—Kris T. Fredrick

(57) ABSTRACT

A method and apparatus for enabling chemical identification of individual particles, cells of molecules by obtaining a Raman spectrum of a particle, cell or molecule as it flows past a sensing point in a flow cytometer. The particles, which may be cells or molecules, are associated with a suitable noble metal colloid or colloidal aggregate. Cellular particles may be associated with gold or silver colloidal particles by ultra-sonic sonification while in a sample preparation reservoir containing the gold or silver colloidal suspension. The colloid associated particles are then hydrodynamically focused into a single file by a fluid control module. The surface-enhance Raman Spectrum of individual particles are obtained by illuminating the particle with a laser as the particle flows past a sensing point and gathering the light that is non-elastically scattered (Raman scattered) by the particle. The surface-enhanced Raman spectrum is then analyzed to identify the particle.

17 Claims, 5 Drawing Sheets

OTHER PUBLICATIONS

On-Line Monitoring of Airborne Chemistry in Levitated Droplets: In-Situ Synthesis and Application of SERS Active Ag-Sols for Trace Analysis by FT-Raman Spectrosmetry; Nikolai Leopold, Michael Haberkorn, Thomas Laurell, Johan Nilsson, Josefa R. Baena and Bernard Lendl; Anal. Chem.; 2003; 75(9) pp. 2166-2171; published by American Chemical Society, Washington DC USA.

Single Molecule Detection Using Surface-Enhanced Raman Scattering (SERS); Katrin Kneipp; Yang Wang; Harald Kneipp; Lev T. Perelman; Irving Itzkan; Ramachandra R. Dasari and Michael S. Feld; Phys. Rev. Lett. 78, 1667-1670 (1997); Published by American Physical Society, College, Park, MD USA.

Ultrasensitive Chemical Analysis by Raman Spectroscopy; Katrin Kneipp; Harald Kneipp; Irving Itzkan; Ramachandra R. Dasari; Michael S. Feld; Chem Rev., Oct. 13, 1999; 99 (10): 2957-76; Published by American Chemical Society, Washington DC USA.

Surface-Enhanced Raman Scattering (SERS) Method and Instrumentation of Genomics and Biomedical Analysis; Journal of Raman Spectroscopy; J. Raman Spectrosc. 30, 785-793 (1999) T. Vo-Dinh 1,; D.L. Stokes 1; G.D. Griffin 1; M. Volkan 1; U.J. Kim 2; M.I. Simon 2; Journal of Raman Spectroscopy, vol. 30, Issue 9, pp. 785-793 (1999); Published by John Wiley & Sons, Ltd., Bognor Regis, England.

Flow Analysis-Based Surface-Enhanced Raman Spectroscopy Exchangeable Microbeads as SERS-Active Surfaces Bernhard Lendl; Horst Ehmoser; Johannes Frank and Ruper Schinder; Applied Spectroscopy, Jul. 1, 2000, vol. 54, No. 7, pp. 1012-1018(7); Published by Society for Applied Spectroscopy, Frederick, MD, USA.

Silver Colloids Impregnating or Coating Bacteria; S. Efrima and B.V. Bronk J. Phys. Chem. B 1998, 102, 5947-5950; Published by American Chemical Society, Washington DC USA.

Surface-Enhanced Raman Spectroscopy in Single Living Cells Using Gold Nanoparticles Katrin Kneipp; Abigail s. Haka, Harald Kneipp; Kamran Badizadegan; Noriko Yoshizawa; Charles Boones; Karen E. Shafer-Peltier; Jason T. Motz; Ramachandra R. Dasari; and Michael S. Feld; Applied Spectroscopy, Feb. 1, 2002, vol. 56, No. 2, pp. 150-154 (5); Published by Society for Applied Spectroscopy, Frederick, MD USA.

Silver-Filled Carbon Nanotubes as Spectroscopic Enhancers; F.J. Garcia-Vidal; J.M. Pitarke; J.B. Pendry; Physical Review B; vol. 58, 6783-6786 (1998); Published by American Physical Society, College Park, MD USA.

* cited by examiner

RAMAN DETECTION BASED FLOW CYTOMETER

FIELD OF THE INVENTION

The present invention relates generally to flow cytometers, and more particularly to portable flow cytometers that use surface-enhanced Raman spectroscopy to identify the specimens that are being counted.

BACKGROUND OF THE INVENTION

Flow cytometry is a well known means of measuring certain physical and chemical characteristics of cells or particles by sensing certain optical properties of the cells or particles as they travel in suspension, one by one past a sensing point. Flow cytometry is widely used in the biological and medical fields.

In a typical flow cytometer, the single file flow of particles is achieved using hydrodynamic focusing of the suspended particles within a sheath fluid. The particles are then individually interrogated by a light beam. In most modern cytometers, the light source is a laser which emits coherent light at a specified wavelength. Each particle interacts with the light beam, and typically the scattered and any emitted fluorescent light produced by each particle is collected. By analyzing the scattered light, physical characteristics such as cell size, shape and internal complexity can be determined. Collecting any emitted fluorescent light also allows any cell component or function that can be detected by a fluorescent compound to be examined.

Traditional flow cytometers only detect elastically scattered light (also known as "Rayleigh scattered light") which does not contain any information about the atomic or molecular structure of the particle. Although such flow cytometers can identify the size and shape, they cannot differentiate between similarly sized, but chemically different molecules or cells, unless the molecules or cells have been tagged with fluorescent markers.

In principle, detecting the in-elastically scattered light (also known as "Raman scattered light") would enable the chemical identification of cells or molecules, as each cell or molecule has a unique Raman spectrum based on its chemical structure. The cross-section for Raman scattering is, however, about 15 orders of magnitude lower than the cross-section for Rayleigh scattering. This means that obtaining the Raman spectrum of an individual particle in a flow cytometer is well beyond the realms of practicality because of the lack of a suitably intense light source and the lack of any suitably sensitive detectors. The Raman cross-section, however, can be dramatically increased by a technique known as surface-enhanced Raman scattering, in which the molecule or particle is placed in contact with a suitably roughened noble metal surface, or in contact with a noble metal colloidal aggregate. Under the right conditions, the cross-section of surface enhance Raman scattering approaches the cross-section for fluorescence emission.

In order for flow cytometers to be able to identify individual particle based primarily on the chemical or molecular structure of the particle, what is needed is an apparatus and method that allows particles or cells in a cytometer to be in a condition that produces a sufficiently large surface-enhanced Raman scattering cross-section so that Raman spectra can be obtained from each particle or cell as it passes the cytometer sensing point. Such a system will allow the individual identification of all cells or particles, no matter how similar in size or shape they are to each other, without any need for fluorescent tagging.

SUMMARY OF THE INVENTION

The present invention relates to methods and apparatus for enabling flow cytometers to identify individual particles primarily by means of their chemical or molecular structure.

In a preferred embodiment of the invention, the chemical identification is achieved by obtaining a Raman spectrum of the particle, which may be an individual cell or molecule, as it flows past a sensing point in a flow cytometer. The particles are associated with a suitable noble metal colloid or colloidal aggregate so that their Raman scattering cross-section is surface-enhanced. The particles are then arranged in single file by a fluid control module capable of creating a hydrodynamically focused flow stream, and a light source illuminates each particle as it flows past a sensing point. Because the Raman cross-section is surface-enhanced, the light source may be a conventional laser. The light that is non-elastically scattered (Raman scattered) by the particle is gathered and the surface-enhanced Raman spectrum recorded using suitable dispersion optics and a suitable detector. The surface-enhanced Raman spectrum may then be analyzed to identify the particle from its molecular structure.

In a preferred embodiment of the present invention, cellular particles are associated with gold or silver colloidal particles by ultra-sonic sonification while in a sample preparation reservoir containing a gold or silver colloidal suspension.

These and other aspects of the invention will be described below in greater detail, and by reference to the attached drawings.

DETAILED DESCRIPTION

The Raman based flow cytometry of the present invention counts individually identified particles within a sample by combining non-destructive, molecule specific Raman spectroscopy with a flow cytometer's ability to sequentially observe individual molecules.

One difficulty in implementing Raman based flow cytometry is that Raman scattering has a very low cross-section, i.e., only a very small percentage of the photons in a light beam focused on a sample are Raman (in-elastically) scattered. The effective Raman cross-section of a sample may, however, be increased by the technique of surface enhanced Raman Scattering, in which each molecule is associated with a noble metal colloid or colloidal aggregate. This association can be done by, for instance, sonification of cells in a noble metal colloidal solution.

The cytometric technique of hydrodynamic focusing may then be used to arrange the prepared molecules in a single file, flowing as a core stream within a fluid sheath, ready for individual interrogation by a light source. Hydrodynamic focusing requires precision pumping and control of the sample and sheath fluids within appropriately designed channels, as described in detail below.

An intense light source, preferably a laser source, may be focused onto the molecules flowing in the cytometer corestream, and the in-elastically scattered light collected, detected and analyzed by Raman spectroscopy. For the identification of the molecules, the detection system needs appropriate wavelength selecting elements that provide sufficient detail of the molecule's characteristic Raman spectrum.

An exemplary embodiment of the present invention, having the elements for performing Raman detection based cytometer on individual molecules will now be discussed in detail by reference to the accompanying drawings in which, as far as possible, like numbers represent like elements.

Figure 1:
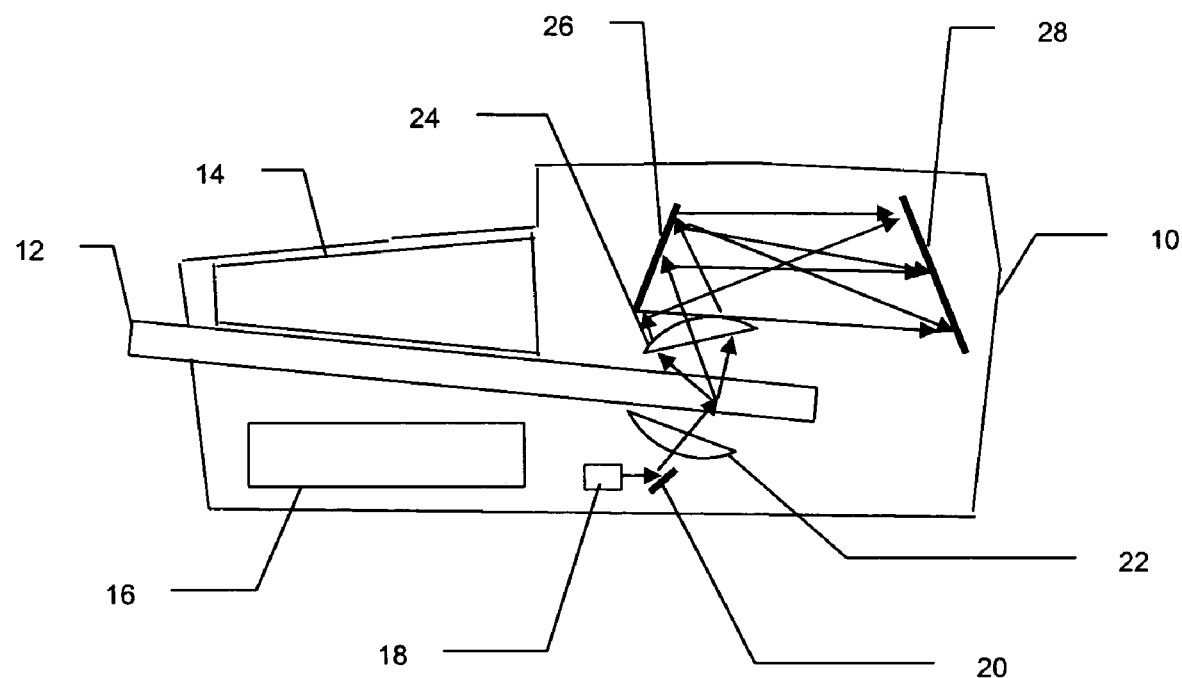
FIG. 1 is a cross-sectional view of an exemplary embodiment of a Raman detection based cytometer.

FIG. 1 is a cross-sectional view of an exemplary embodiment of a Raman detection based flow cytometer, comprising an instrument housing 10, a removable cartridge 12, a pressurization module 14, control electronics 16, an illumination source 18, source steering optics 20, source focusing optics 22, Raman scattered light collecting optics 24, a light dispersing optical element 26 and a light detecting element 28.

Figure 2:
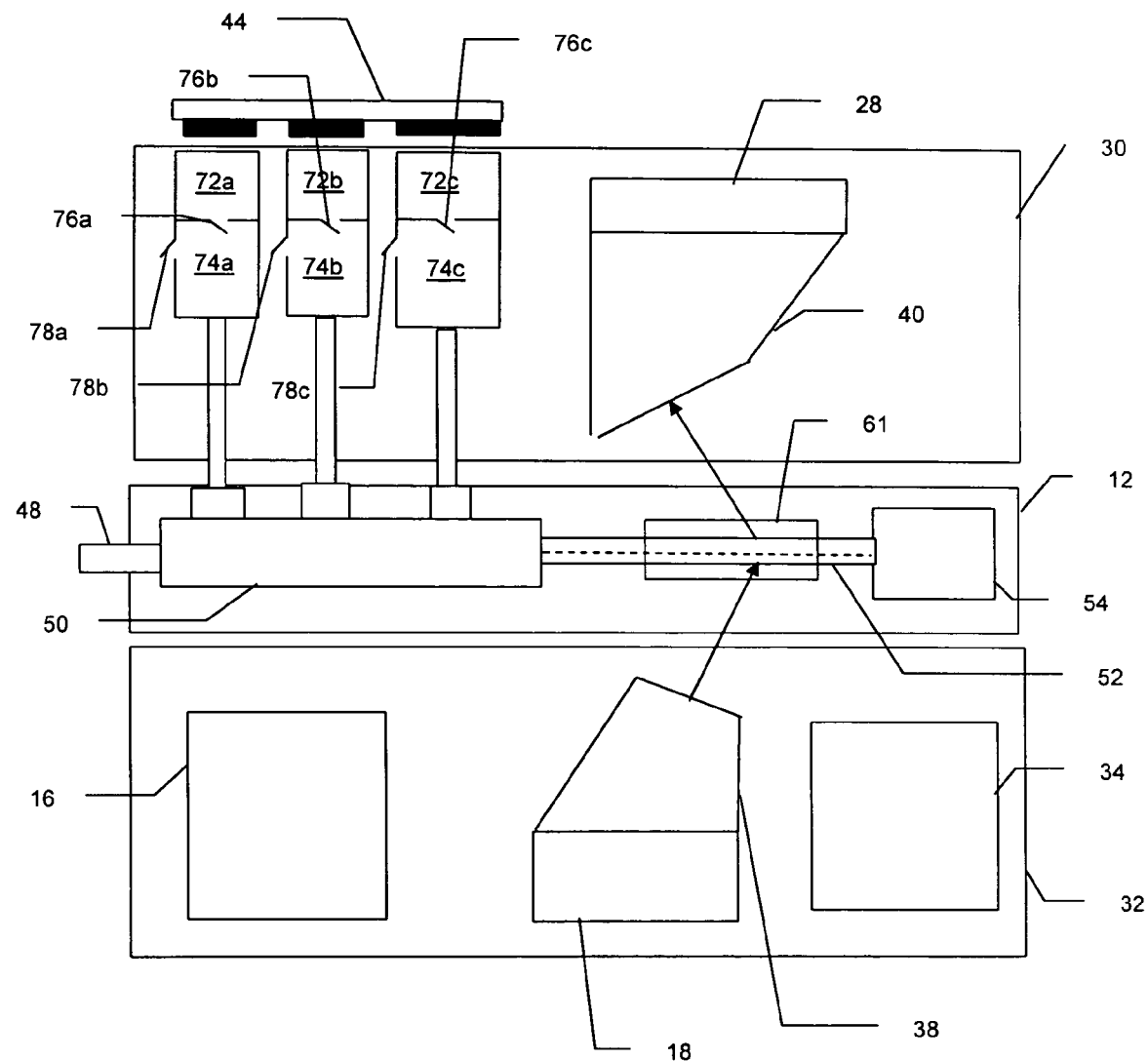
FIG. 2 is a schematic view of an exemplary embodiment of a Raman detection based cytometer.

FIG. 2 is a schematic view of an exemplary, portable embodiment of a Raman detection based flow cytometer, comprising a lower section 32 having batteries 34, illumination source 18, illumination steering and collimating optics module 38, control electronics 16; an upper section 30, comprising a scattered light detection and dispersion module 40, a light detecting element 28, a manual pressurizing unit 44, first pressure chambers 72a, 72b and 72c, second pressure chambers 74a, 74b and 74c, first valves 76a, 76b and 76c and second set of valves 78a, 78b and 78c; and a removable cartridge 12, comprising a sample supply lumen 48, a fluid control unit 50, a flow stream 52, a Raman chamber 61 and a waste reservoir 54. The removable cartridge 12 may be made primarily of materials such as molded plastic that allow the cartridge to be mass produced and disposable.

Figure 3:
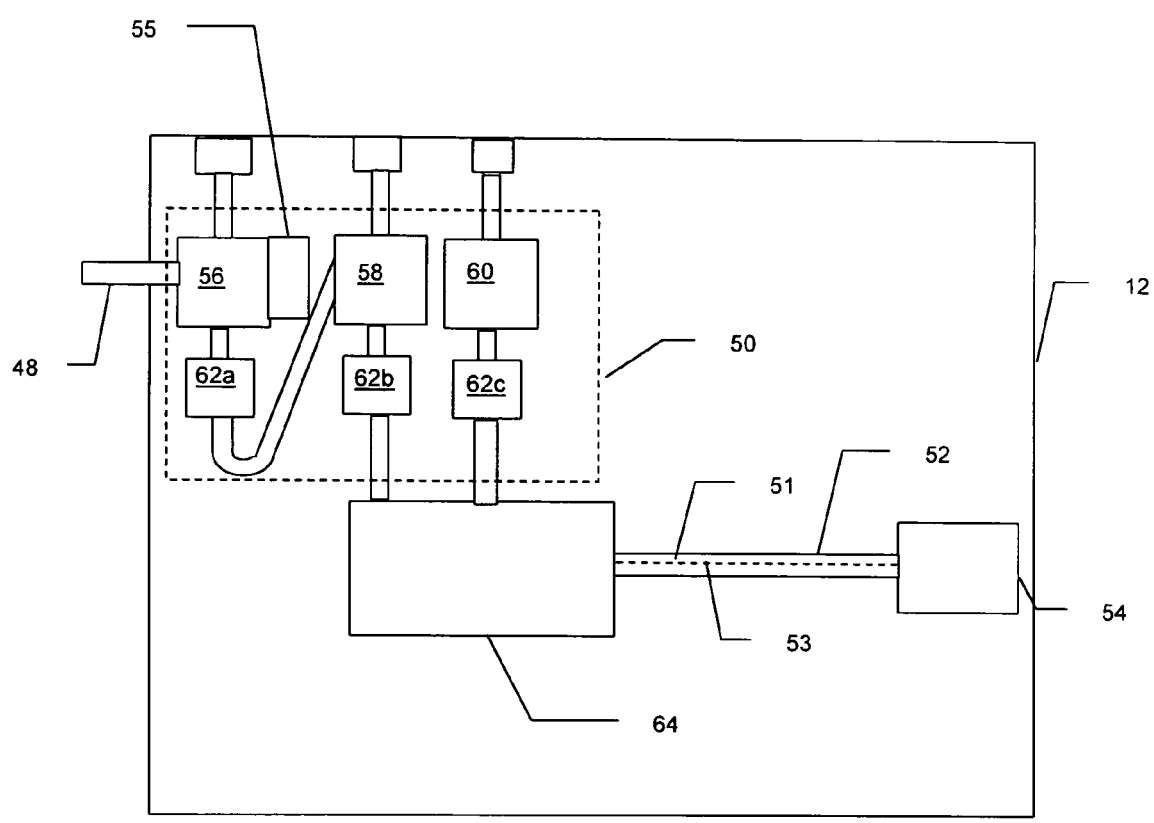
FIG. 3 is a schematic view of an exemplary embodiment of a removable cartridge of the present invention.

FIG. 3 is a schematic view of an exemplary embodiment of a removable cartridge 12 of the present invention, in which the fluid control unit 50 comprises an ultrasonic source 55, a sample conditioning reservoir 56, a sample storage reservoir 58, a sheath fluid reservoir 60, flow sensors 62a, 62b and 62c, a hydrodynamic focusing module 64, a flow channel 52 in which a sheath fluid 51 surrounds a core stream 51.

The sample may be prepared off-line or in the sample conditioning reservoir 56. Examples of sample preparation techniques that enhance the Raman cross-section of molecules include loading cells with colloidal gold by fluid-phase uptake or sonification, as described in detail in, for instance, in the article entitled "Surface-Enhanced Raman Spectroscopy in Single Living Cells Using Gold Nanoparticles", by Kneipp et al, Applied Spectroscopy, Volume 56, number 2, 2002, pp 150-154, the contents of which are hereby incorporated by reference. The molecules may also have enhanced Raman cross-sections by attaching them to micro-beads filled with noble-metal (copper, gold, silver, platinum, palladium and iridium) colloids, as described in, for instance, in the article entitled "Flow Analysis-based Surface-Enhanced Raman Spectroscopy Employing Exchangable Microbeads as SERS-active Surfaces" by Lendl et al. in Applied Spectroscopy, Volume 54, number 7, 2000, pp 1012-1018, the contents of which are hereby incorporated by reference. Noble metal colloids can also be made to aggregate into clusters suitable for individual molecules to attach to, as described in detail in, for instance, the article, "Single Molecule Detection Using Surface Enhanced-Raman Scattering (SERS)" by Kneip et al. in Physical Review Letters, volume 78, number 9, 1997, pp 1667-1670, the contents of which are hereby incorporated by reference. Molecules may also be attached to microstructures, such as liposomes, that are filled or coated with noble metal colloids. Molecules themselves may also be coated with noble metal colloids. Other possible methods for associating the cellular particles with the nobel metal colloidal particles include, but are not limited to, the manual injection of the metal colloids into individual cells and treating the metal colloidal particles as projectiles and firing them into the cellular particles.

In a preferred embodiment, intended for Raman based cytometry of individual cells, the sample conditioning reservoir 56 is adjacent to an ultrasonic source 55, which may be controlled by control electronics 16. The sample conditioning reservoir 56 comprises a cell supporting, buffer solution containing aggregated clusters of 60 nm gold nanoparticles. Once sample cells have been fed into the buffer solution, a short burst of ultrasound ruptures the cell membrane, permitting gold colloid uptake by the cell. On cessation of the ultrasound, the cell membrane typically self-anneals within seconds.

The prepared sample fluid is then fed from the sample conditioning reservoir 56 into the sample storage reservoir 58. The sample fluid is then fed into the hydrodynamic focusing module 64, which may be a fluidic circuit engineered to perform hydrodynamic focusing, as described in detail in, for instance, U.S. Pat. No. 6,597,438, titled "Portable Flow Cytometery" issued to Cabuz et al. on Jul. 22, 2003, the contents of which are hereby incorporated by reference. The hydrodynamic focusing causes molecules of the sample to fall into single file a long a core stream 53 surrounded by a sheath fluid 51 within the flow channel 52. The velocity of the sheath fluid 51 is preferably about 9 times that of the core stream 53. Additionally, the velocity of the sheath fluid 51 and the core stream 53 remain sufficiently low to maintain laminar flow in the flow channel 52.

In a preferred embodiment, the required velocity of the sheath fluid and the sample fluid are provided by a combination of a manual pressurizing unit 44, coupled via pressure chambers 46b and 46c to fluid reservoirs 58 and 60 and fluid flow sensors 62b and 62c, all acting in a closed feed-back loop under control electronics 16.

The manual pressurizing unit 44 may, for instance, be manually powered plungers or bulbs with a check valve. In either case, the manually generated pressure is preferably provided to first pressure chambers 72a, 72b and 72c. First valves 76a, 76b and 76b are then provided for controllably releasing the pressure in the first chambers 72a, 72b and 72c to the second pressure chambers 74a, 74b and 74c. Second valves 78a, 78b and 78c may be provided in the second pressure chambers 74a, 74b and 74c for controllably venting the pressure in the second pressure chambers 74a, 74b and 74c. The control electronics 16, which typically comprises a programmable micro-processor, opens the first valves 76a, 76b or 76c when the fluid flow in the corresponding downstream fluid stream drops below a first predetermined value and opens the second, vent value 78a, 78b or 78c when the fluid flow in the downstream fluid increases above a second predetermined value. Each value is preferably an array of electrostatically actuated micro-valves that are individually addressable and controllable. The fluid flow sensors 62a, 62b and 62c are preferably thermal anemometer type flow sensors.

The hydrodynamically focused core stream 53, containing sample particles arranged in single file, surrounded by a sheath fluid 51, flows through flow channel 52 into Raman chamber 61.

Figure 4:
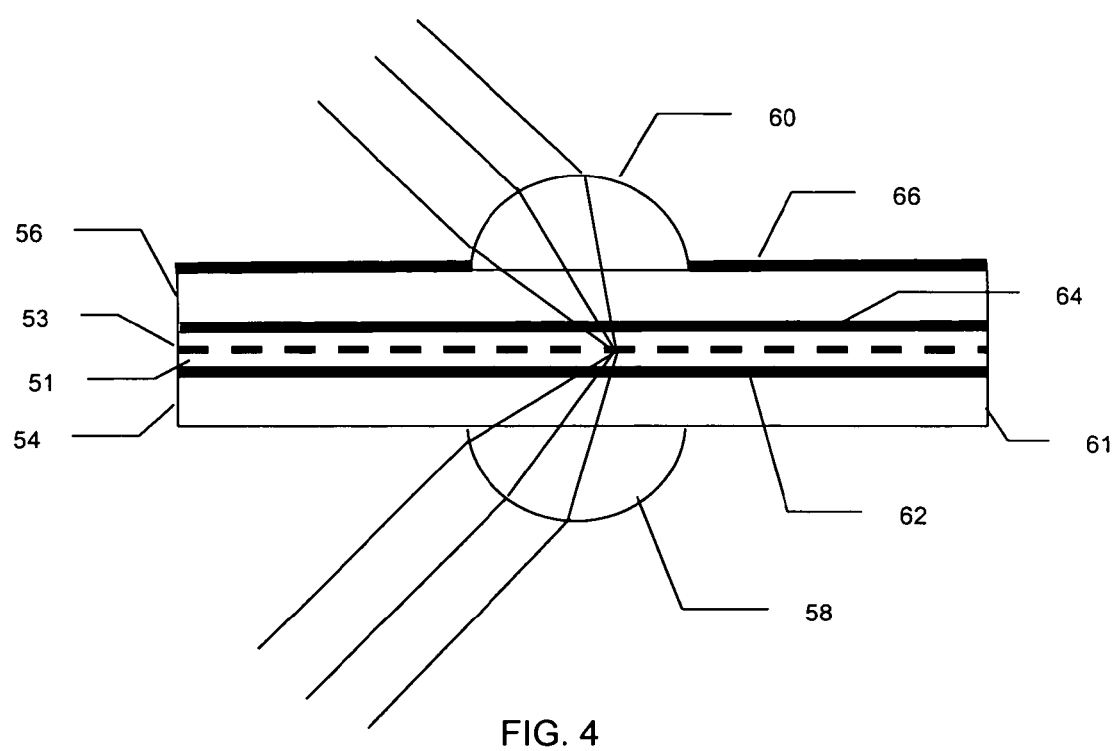
FIG. 4 is a cross-sectional view of the cytometer flow channel of an exemplary embodiment of a Raman detection based cytometer.

FIG. 4 is a cross-sectional view of the cytometer flow channel of an exemplary embodiment of a Raman detection based cytometer, comprising the flow stream 52, an upper and a lower glass substrate 56 and 54, an illuminating micro-lens 58, a detecting micro-lens 60, a source pass filter and source absorbing filters 64 and 66, a focused core stream 53, containing sample particles.

Figure 5:
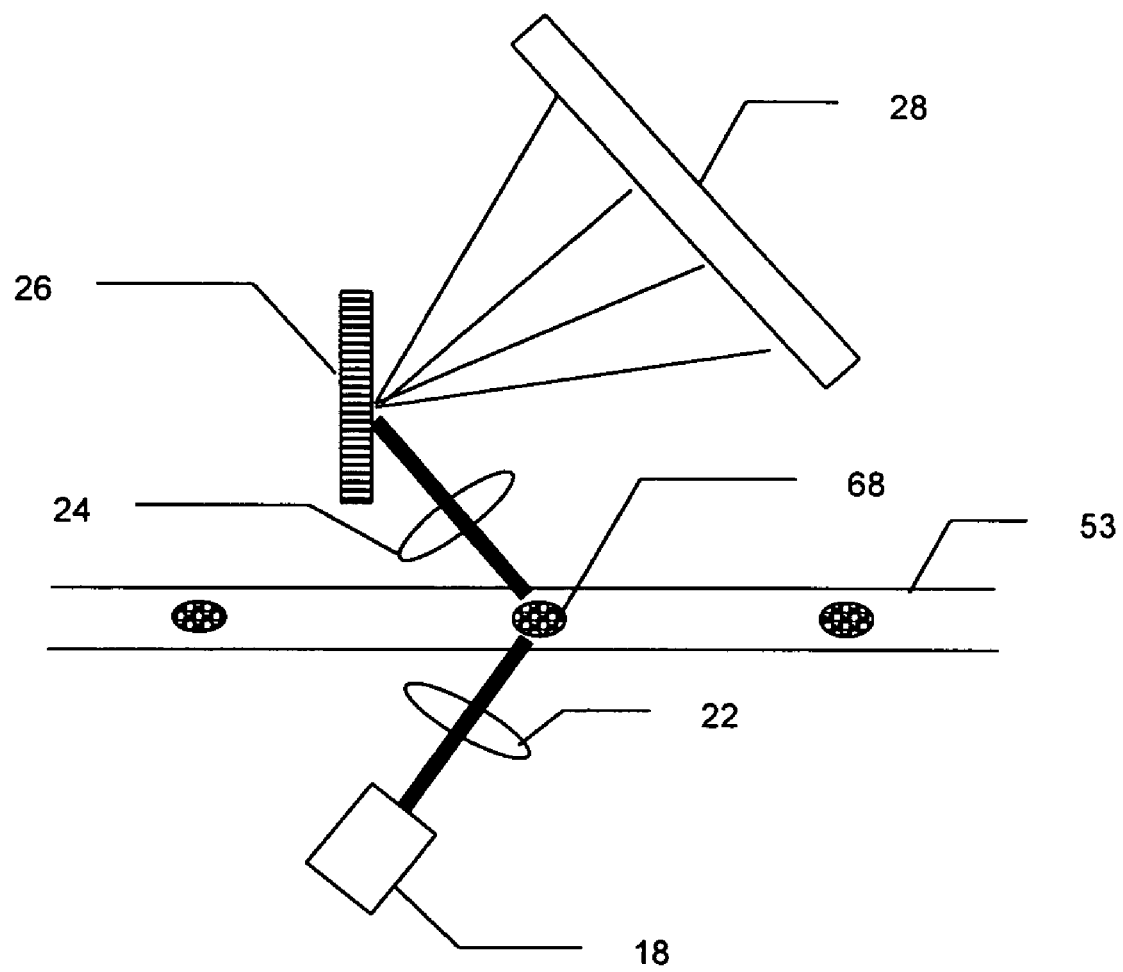
FIG. 5 is a schematic view of the illumination and detection optics of an exemplary embodiment of a Raman detection based cytometer.

FIG. 5 is a schematic view of the illumination and detection optics of an exemplary embodiment of a Raman detection based cytometer, comprising an illumination source 18, source focusing optics 22, a focused core stream 53 containing sample particles 68, Raman-scattered light-collecting optics 24, a light dispersing optical element 26 and a light detecting element 28.

In a preferred embodiment, the Raman chamber 61 comprises glass substrates 56 and 54, flow channel 52, micro-lenses 58 and 60, source-pass filter 62, and source-absorbing filter 64 and 66.

Light emitted by light source 18 is directed as a collimated beam onto micro-lens 58 by beam steering and collimating optics 38. Micro-lens 58 focuses the light though source-pass filter 62 onto particles in the core stream 53. Light that is in-elastically (Raman) scattered from particle in the core stream 42 passes through source-absorbing filter 56 and is directed towards detector 28 by micro-lens 60 and steering and discrimination optics 40.

Light source 18 may be a laser or array of lasers having a wavelength, a power and a polarization suitable for Raman spectroscopy. Prior art light sources include argon-ion pumped Ti:sapphire lasers operating at 830 nm, providing 200 mW of power focused down to about $2 \times 10^5$ W/cm$^2$ at the sample. Other suitable light sources include Nd:Yag laser operating at 1064 nm and helium neon lasers operating at 632.8 nm. A Vertical Cavity Surface Emitting Laser (VCSEL) is particularly suited to portable implementation. VCSEL are available that operate at wavelengths in the range from 850 nm to 670 nm. A 10×10 micron emitting surface VCSEL typically has a power of about 1 mW, producing a power density of about $1 \times 10^3$ W/cm$^2$ when focused to a Gaussian spot of about 10 microns. Any suitable solid state laser may be used as light source 18.

The light source 18 may also be a single light source, such as a solid state laser or a diode laser, movably attached to one or more stepper motors so that either the sources lateral position or distance from the core-stream 53, or both, may be adjusted to achieve optimal scattering. Adjustment of such a movable source in focus and/or lateral displacement with respect to the core stream 53 may include a feed-back loop responsive to light reflected by a difference in refractive index between the core stream 53 and the sheath fluid 51. The adjustment feed-back loop may also be accomplished by, for instance, using light reflected or scattered from tracking or calibration micro-beads that are interspersed with the molecules of interest in the core-stream Steering and discrimination optics 40 and detector 28 may be, for instance, a Sentinal Raman Spectrometer having a Charge Couple Device detector (CCD), as supplied by Bruker Optics, Inc. of Bilerica, Mass. Detector 28 may also be any other low noise, high quantum efficiency multichannel detector or CCD array. Steering and discrimination optic module may also comprise any suitable combination of filters, acoustoptic tunable filters (AOTF), gratings, diffraction optics and holographic optics. In a preferred embodiment, the steering and discrimination optic module is a suitable holographic diffraction grating that combines wavelength selection with focusing the collected Raman scattered light onto the detector 28.

Source-pass filter 62 is a coating that band passes only the source wavelength, thereby eliminating collecting Raman scattered light that occurs before the flow channel. Any suitable well-know multi-layer or holographic band pass filter may be used.

Source-absorbing filters 64 and 66 are coatings that reject the source wavelength, thereby eliminating Raman scattering after the flow channel. Any suitable well-known multi-layer or holographic band pass filter may be used.

Once the core stream 53 and surrounding sheath fluid 51 have passed through Raman chamber 61, they drain into waste reservoir 54.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

What is claimed is:

1. An apparatus for identifying a molecule, comprising:
    a fluid control module capable of creating a hydrodynamically focused flow stream containing a molecule, said molecule associated with a metal colloid;
    a light source capable of illuminating said molecule;
    a sonicator capable of incorporating said metal colloid into said molecule; and
    a detector capable of detecting light that is non-elastically scattered from said molecule.

2. The apparatus of claim 1 further comprising an analyzing module capable of analyzing said detected light to identify said molecule.

3. The apparatus of claim 1 further comprising an instrument housing; and wherein said fluid control module further comprises a cartridge that is removable from said instrument housing, and wherein said hydrodynamically focused flow stream occurs on said removable cartridge.

4. The apparatus of claim 1 wherein said light source is a solid state laser.

5. The apparatus of claim 4 wherein said solid state laser is a red Vertical Cavity Surface Emitting Laser (VCSEL) device focused onto said molecule, thereby providing said non-elastically scattered ray of light.

6. An apparatus for identifying a molecule, comprising:
    a fluid control module capable of creating a hydrodynamically focused flow stream containing a molecule;
    a light source capable of illuminating said molecule; and
    a detector capable of detecting light that is non-elastically scattered from said molecule, wherein said detector further comprises an acousto-optic tunable filter (AOTF).

7. An apparatus for identifying a molecule, comprising:
    a fluid control module capable of creating a hydrodynamically focused flow stream containing a molecule;
    a light source capable of illuminating said molecule;
    a detector capable of detecting light that is non-elastically scattered from said molecule; and an analyzing module capable of analyzing said detected light to identify said molecule, wherein said analyzing module further comprises a data-base comprising a surface enhanced Raman spectrum (SERS) of a representative molecule.

8. A method of identifying a molecule, comprising the steps of:
associating a metal with said molecule by incorporating said metal, in colloidal form, into said molecule by one or more of fluid-phase uptake and sonification;
positioning said molecule in a hydrodynamically focused flow stream;
illuminating said molecule with a predetermined wavelength of light; and
detecting non-elastically scattered light from said molecule.

9. The method of claim 8 further comprising analyzing said detected non-elastically scattered light to identify said molecule.

10. The method of claim 8 wherein said illuminating step occurs while said molecule is in said hydrodynamically focused flow.

11. The method of claim 8 wherein said metal colloid is chosen from the group consisting of copper, gold, silver, platinum, palladium and iridium.

12. The method of claim 8 wherein said associating step further comprises attaching said molecule to one or more of a metal colloid aggregate, a metal colloid coated bead, a metal colloid filled liposome and a metal colloid infused bead.

13. The method of claim 8 further comprising the steps of:
providing an instrument housing; and
providing a cartridge that is removable from said instrument housing, and wherein said hydrodynamically focused flow stream occurs on said removable cartridge.

14. The method of claim 8, wherein said illuminating step utilizes a laser.

15. The method of claim 8, wherein said laser is a red Vertical Cavity Surface Emitting Laser (VCSEL) device.

16. A method of identifying a molecule, comprising the steps of:
positioning said molecule in a hydrodynamically focused flow stream;
illuminating said molecule with a predetermined wavelength of light; and
detecting non-elastically scattered light from said molecule, wherein said detecting step utilizes a wavelength discriminating device chosen from the group consisting of a prism, a diffraction grating, a thin film filter, an absorption filter and an acousto-optic tunable filter (AOTF), or a combination thereof.

17. A method of identifying a molecule, comprising the steps of:
positioning said molecule in a hydrodynamically focused flow stream;
illuminating said molecule with a predetermined wavelength of light;
detecting non-elastically scattered light from said molecule; and
analyzing said detected non-elastically scattered light to identify said molecule, wherein said analyzing step includes using a data-base comprising a surface enhanced Raman spectrum (SERS) of a representative molecule.

* * * * *